(12) United States Patent
Nielsen Groot

(10) Patent No.: US 8,540,425 B2
(45) Date of Patent: Sep. 24, 2013

(54) CT SCANNING SYSTEM

(75) Inventor: Gorm Nielsen Groot, Vedbaek (DK)

(73) Assignee: GNI APS, Horsholm (DK)

( * ) Notice: Subject to any disclaimer, the term of this patent is extended or adjusted under 35 U.S.C. 154(b) by 297 days.

(21) Appl. No.: 12/996,334

(22) PCT Filed: May 29, 2009

(86) PCT No.: PCT/EP2009/003846
§ 371 (c)(1),
(2), (4) Date: Jan. 25, 2011

(87) PCT Pub. No.: WO2009/146851
PCT Pub. Date: Dec. 10, 2009

(65) Prior Publication Data
US 2011/0150177 A1  Jun. 23, 2011

(30) Foreign Application Priority Data
Jun. 6, 2008 (EP) .................................... 08010336

(51) Int. Cl.
*H01J 35/16* (2006.01)

(52) U.S. Cl.
USPC ........................................................ 378/203

(58) Field of Classification Search
USPC ............................ 378/203; 250/515.1, 517.1
See application file for complete search history.

(56) References Cited

U.S. PATENT DOCUMENTS

| 5,604,784 | A | 2/1997 | Widlicka | |
|---|---|---|---|---|
| 6,448,571 | B1 * | 9/2002 | Goldstein | .................. 250/515.1 |
| 6,653,648 | B2 * | 11/2003 | Goldstein | .................. 250/515.1 |
| 2004/0161076 | A1 | 8/2004 | Goldstein | |
| 2005/0166808 | A1 | 8/2005 | Keil | |
| 2005/0236588 | A1 * | 10/2005 | Ein-Gal | ...................... 250/515.1 |
| 2009/0110152 | A1 * | 4/2009 | Manzke et al. | ................ 378/203 |

FOREIGN PATENT DOCUMENTS

| WO | 2005022195 A | 3/2005 |
|---|---|---|
| WO | 2005102174 A | 11/2005 |
| WO | 2007060561 A | 5/2007 |

OTHER PUBLICATIONS

International Search Report for PCT/EP2009/003846, Sep. 2, 2009.
Written Opinion for PCT/EP2009/003846, Sep. 2, 2009.
International Preliminary Report on Patentability for PCT/EP2009/003846, Aug. 10, 2010.

* cited by examiner

*Primary Examiner* — Glen Kao
(74) *Attorney, Agent, or Firm* — Brinks Hofer Gilson & Lione

(57) ABSTRACT

A CT scanning system having a patient table and a gantry comprising an x-ray source configured to irradiate an x-ray beam while at least partly rotating about an object being arranged on the patient table in order to be scanned. The gantry comprises an x-ray detector configured to receive x-rays penetrating through the object to be scanned and is further configured to provide output signals representative of the received x-rays. The system further comprises an x-ray cabinet comprising x-ray shielding material. The x-ray cabinet fully surrounds the gantry and the patient table. The patient table is configured to be fully inserted in the x-ray cabinet. The x-ray cabinet has an end part with a patient opening allowing the introduction of a patient into the x-ray cabinet through said opening. The system comprises a closure part for providing an x-ray shielding closure of the patient opening at the first end part.

20 Claims, 7 Drawing Sheets

CT SCANNING SYSTEM

RELATED APPLICATIONS

This application claims the benefit under 35 U.S.C. §371 of International Patent Application No. PCT/EP2009/003846, filed May 29, 2009, which claims priority to European Patent Application No. 08010336.9, filed Jun. 6, 2008, the contents of all of which are incorporated herein by reference in their entirety.

FIELD OF THE INVENTION

The invention relates generally to a computer tomographic (CT) x-ray scanning system, and more particularly to CT scanning system having an x-ray shielded cabinet. The system of the invention may advantageously be used in veterinary clinics or hospitals, especially for CT-scanning of cats, dogs and other pets.

DESCRIPTION OF THE PRIOR ART

Computerized tomography (CT) is a diagnostic technique known for human use dated back to the early 1970's. With the use of an x-ray tube, an x-ray detector (x-ray camera) and a computer, it is possible to create pictures of multiple, thin, transverse sections of a patient's body. In CT-scanning many axial (cross-sectional) two-dimensional images are reconstructed by computer analysis of transmitted x-ray intensity. This results in a focused, detailed view of the region of interest at the patient.

In the conventional helical-scanning type of a CT scanner, a table top of a patient couch mounting the object to be scanned thereon is continuously moved at a regular speed in an x-ray CT gantry dome. However, CT scanners are known in which the x-ray gantry is moved along the patient table, whereby the object on the patient table can be scanned without being moved. Such CT scanners are known from U.S. Pat. No. Re. 36,099, U.S. Pat. No. 5,109,397, U.S. Pat. No. 6,840,673, and U.S. Pat. No. 6,212,251.

The conventional large-scale CT scanners may require a special, high power electrical outlet, such as a three-phase AC outlet. But CT scanners being driven by rechargeable batteries for making the system capable of being operated from 110/220 volt AC power have been described in U.S. Pat. No. 5,226,064, U.S. Pat. No. 5,808,376, and U.S. Pat. No. Re. 35,025.

Large-scale CT scanners are usually located in the x-ray department of hospitals and are housed in expensive shielded rooms, but a self-shielded CT scanner has been proposed in U.S. Pat. No. 4,977,585. Here, the scanner has a patient tunnel in which the walls and the ends of the patient tunnel include shielding material to form a shielded enclosure in which the patient body portion is scanned. However, the shielded patient tunnel is shorter than the patient and it is only a part of the patient, which is inside the tunnel, leading to a problem of having an efficient shielding of the ends of the patient tunnel.

The veterinary today faces many diagnostic challenges, which can only be solved by CT-scanning. It is difficult for a veterinary clinic to invest in a large-scale standard human CT-scanner. The total cost of ownership is too high and therefore there is no—or in best case a weak and risk-full business case if purchasing a human CT-scanner for veterinary use. This might be the reason why the human CT-scanner is rarely seen in veterinary hospitals or clinics.

Thus, there is a need for a CT scanning system specially designed to fulfil the needs of veterinary clinics or hospitals including lower cost when compared to existing human CT scanners.

SUMMARY OF THE INVENTION

According to the present invention, there is provided a CT scanning system comprising: a patient table; a gantry comprising an x-ray source configured to irradiate an x-ray beam while at least partly rotating about an object being arranged on the patient table in order to be scanned, said gantry further comprising an x-ray detector configured to receive x-rays penetrating through the object to be scanned and further configured to provide output signals representative of the received x-rays; and an x-ray cabinet comprising x-ray shielding material. It is preferred that the x-ray cabinet is fully surrounding the gantry. The x-ray cabinet may at least partly surround the patient table. However, it is preferred that the x-ray cabinet is fully surrounding the patient table. Thus, it is within an embodiment of the invention that the patient table is configured to be at least partly or fully inserted in the x-ray cabinet.

Here it should be understood that the expression patient table preferably refers to a bed or couch on which the object to be scanned is resting during a scanning operation. According to an embodiment of the present invention, the whole body of the object to be scanned may be arranged inside the x-ray cabinet during a scanning operation, and when referring to the patient table being fully surrounded by the x-ray cabinet it is the part of the table, bed or couch, on which the object to be scanned is resting, that is fully inserted in the x-ray cabinet and thereby fully surrounded by the x-ray cabinet.

According to an embodiment of the invention, the x-ray cabinet may have an end part with a patient opening allowing the introduction of a patient into the x-ray cabinet through said opening. Preferably, the CT scanning system of the invention may further comprise a closure part or door for providing an x-ray shielding closure of the patient opening at the first end part.

It is within one or more embodiments of the invention that one or more access panels are provided in the x-ray cabinet, said access panel(s) requiring tools to be opened and being designed to be removed or opened for maintenance or service purposes.

It is preferred that the x-ray cabinet is substantially tubular or cylindrical, but is also within the invention that the cabinet has other forms, such as an elliptical, square or rectangular end form. It is also preferred that the x-ray cabinet has an elongated form.

The x-ray cabinet may have first and second oppositely arranged end wall parts, and the patient opening may be arranged in the first of said end wall parts.

According to an embodiment of the invention, the x-ray cabinet has a window formed by an x-ray shielding material.

It is within one or more embodiments of the invention that the x-ray cabinet is formed by at least two parts. Here, the x-ray cabinet may be formed by two substantially mirrored parts, each of said mirrored parts holding about half of the patient opening. Preferably, each of the parts forming the x-ray cabinet is dimensioned so as to be able to pass through a standard indoor office door.

It should be understood that according to the principles of the present invention, the x-ray cabinet may be dimensioned in accordance with the size of the objects to be scanned, which objects are to be fully inserted into the x-ray cabinet.

According to an embodiment of the invention, the patient opening may have a width or a diameter of at least 200 mm, such as of at least 400 mm, such as around 500 mm. It is also within one or more embodiments of the invention that the patient opening has a width or a diameter not larger than 800 mm.

The invention covers embodiment in which the x-ray cabinet has a width or a diameter of at least 700 mm, such as of least 1000 mm, such as of at least 1600 mm, such as of at least 2000 mm. Preferably, the x-ray cabinet has a width or a diameter not larger than 2500 mm.

The invention also covers embodiments in which the x-ray cabinet has a length of at least 600 mm, such as of at least 1000 mm, such as of at least 1500 mm, such as in the range of 1800-2000 mm. Preferably, the x-ray cabinet has a length not larger than 3000 mm.

The present invention covers embodiments wherein the x-ray cabinet wall parts comprise a layer of lead or tungsten for obtaining said x-ray shielding. It is also within embodiments of the invention that the closure part or door comprises a layer of lead or tungsten for obtaining said x-ray shielding, and that the window comprises lead or tungsten for obtaining said x-ray shielding. However, it is also within the scope of the invention that other suitable materials may be used for obtaining the x-ray shielding effect.

It is within an embodiment of the invention that the x-ray cabinet is arranged on a support structure to thereby be lifted or arranged at a distance above the ground floor. Here, the x-ray cabinet may be supported by a number of machine mounts for levelling the x-ray cabinet.

It is preferred that the closure part or door is connected to a first end part of the patient table. It is also preferred that the patient table comprises at least two carbon fiber tubes for support of the object to be scanned. Here, the carbon fiber tubes may be made of a near radiation transparent carbon fiber material having a linear attenuation coefficient below 10.000 Hounsfield units, HU, such as below 5000 HU, such as below 3000 HU, such as below 2000 HU. It is also preferred that the patient table comprises a tarpaulin extending between the two carbon fiber tubes for support of the object to be scanned. According to an embodiment of the invention the patient table has an elongated form.

According to an embodiment of the invention, the patient table is supported by a mobile undercarriage, whereby the patient table can be moved into and out of the patient opening. Here, when the x-ray cabinet is arranged on a support structure to thereby be lifted at a distance above the ground floor, the undercarriage or lower part of the undercarriage may be configured to be positioned beneath the x-ray cabinet when the patient table is moved into the patient opening and arranged inside the x-ray cabinet. It is preferred that the closure part or door and the undercarriage is connected to the patient table at the same end part of the patient table.

It is within an embodiment of the invention that there is provided an opening in the closure part, which opening leads into an x-ray shielded pipe arranged on the outer side of the closure part, whereby cables and/or tubes can be fed through the closure part. The closure part or door may be provided with an interlock function being active only when the closure part or door is in a closing position relative to the patient opening or door of the x-ray cabinet. Thus, it is preferred that the interlock function is configured so that an x-ray scanning function can be performed only when the interlock function is active. The present invention covers different embodiments for the interlock function, such as obtaining the interlock function by use of a magnetic or mechanical contact.

The present invention also covers one or more embodiments, wherein the CT scanning system further comprises: a battery charger for receiving electrical power from an external power source, and for providing a regulated DC power signal; a rechargeable battery assembly for storing electrical energy received via the regulated DC power signal; and a high voltage generator for supplying electrical power to the x-ray source during a scanning operation. Here, the rechargeable battery assembly may be adapted for supplying electrical energy to the high voltage generator during the scanning operation. The high voltage generator may be adapted for generating a voltage in the range of 30.000-140.000 Volts for the supply of electrical power to the x-ray source, and the high voltage generator may be adapted for providing electrical power in the range of 500 W to 10 KW for the supply of electrical power to the x-ray source. The battery assembly may be dimensioned for storing an amount of electrical energy being sufficient to feed the high voltage generator for the completion of a scanning operation without interruption. Thus the battery assembly may comprise a sufficient number of rechargeable batteries for storing said amount of electrical energy, such as at least 12 or at least 16 rechargeable batteries. It is preferred that the CT scanning system further comprises a filter assembly inserted between the external power source and the battery charger.

The present invention also covers one or more embodiments, wherein the CT scanning system further comprises a linear moving system for moving the gantry along a substantial portion of the patient table, when the patient table is inserted in the x-ray cabinet. Here, the linear moving system may be adapted for moving the gantry in a direction substantially perpendicular to the rotational movement direction of the x-ray source. It is preferred that the CT scanning system is adapted for performing a scanning operation while rotating the x-ray source about the patient table during a time period when there is no movement of the gantry by the linear moving system. Here, the CT scanning system may be adapted for rotating the x-ray source at an angle in the range of 170-190° such as about 180° when performing said scanning operation in the time period of no movement of the gantry by the linear moving system. According to an embodiment of the invention the gantry comprises a stator part and a rotor part, where the rotor part holds the x-ray source and is adapted for rotating at an angle of at least 170° or of at least 180° during a scanning operation.

It is within one or more embodiments of the invention that the linear moving system is adapted for moving the gantry along the patient table in successive steps, and that the CT scanning system is adapted for performing a scanning operation after each said movement steps, whereby a layered scanning of the object to be scanned can be accomplished. Here, the linear moving system may be adapted for moving the gantry along the patient table in steps of a length being in the range of 10-50 mm, such as in the range of 20-30 mm, such as about 25 mm. It is also within one or more embodiments of the invention that the CT scanning system is adapted for rotating the x-ray source at a rotational speed being in the range of 0.3-30 rpm, such as in the range of 0.3-10 rpm, such as in the range of 0.5-5 rpm, such as about 0.7 rpm when performing said scanning operation in the time period of no movement of the gantry by the linear moving system.

The present invention further covers an embodiment, wherein the x-ray detector has a number of detector elements arranged to form a curved shape opposite the x-ray source, and the x-ray source has an x-ray tube with the dimension of the focal spot being chosen so that the system is working optimal at the centrally arranged detector elements with a decrease of the scanning resolution for the detector elements arranged out to the rim of the curved shape of detector elements.

It should be understood that when using the principles of the present invention, it is possible to produce a CT-scanner, which may be specially designed to meet the needs of the veterinarians at an affordable price level. Such a veterinary CT-scanner may, when compared to existing human CT-scanners, have the following benefits:

Lower total cost of ownership (lower purchasing, installation, implementation, operating and maintenance costs)

Due to the x-ray cabinet with radiation shield there is no need to secure the room in regards to radiation, as the unit may be classified as an x-ray cabinet.

For CT scanners having a rechargeable power supply unit it is possible to use standard power outlet.

Quick installation and commissioning (the CT scanner may be installed and in use at a clinic in one to two days).

Easy to operate (may require less training for operating personal—thus a clinic may be less dependent on one or few trained operators).

Lower weight and operating space, which makes it possible to install the CT scanner on the floor in a standard clinic/office room.

For CT scanners with a lead window, the veterinary can stay close to the CT-scanner and observe the animal through the window during scanning.

Short distance between animal and surveillance/medical supply equipment.

For CT scanners with a movable patient table, it is possible to have more than one patient table and thereby it is possible to increase the use of the CT-scanner (when scanning one animal another animal can at the same time be prepared for scanning on another patient table).

DETAILED DESCRIPTION OF THE INVENTION

Figure 1:
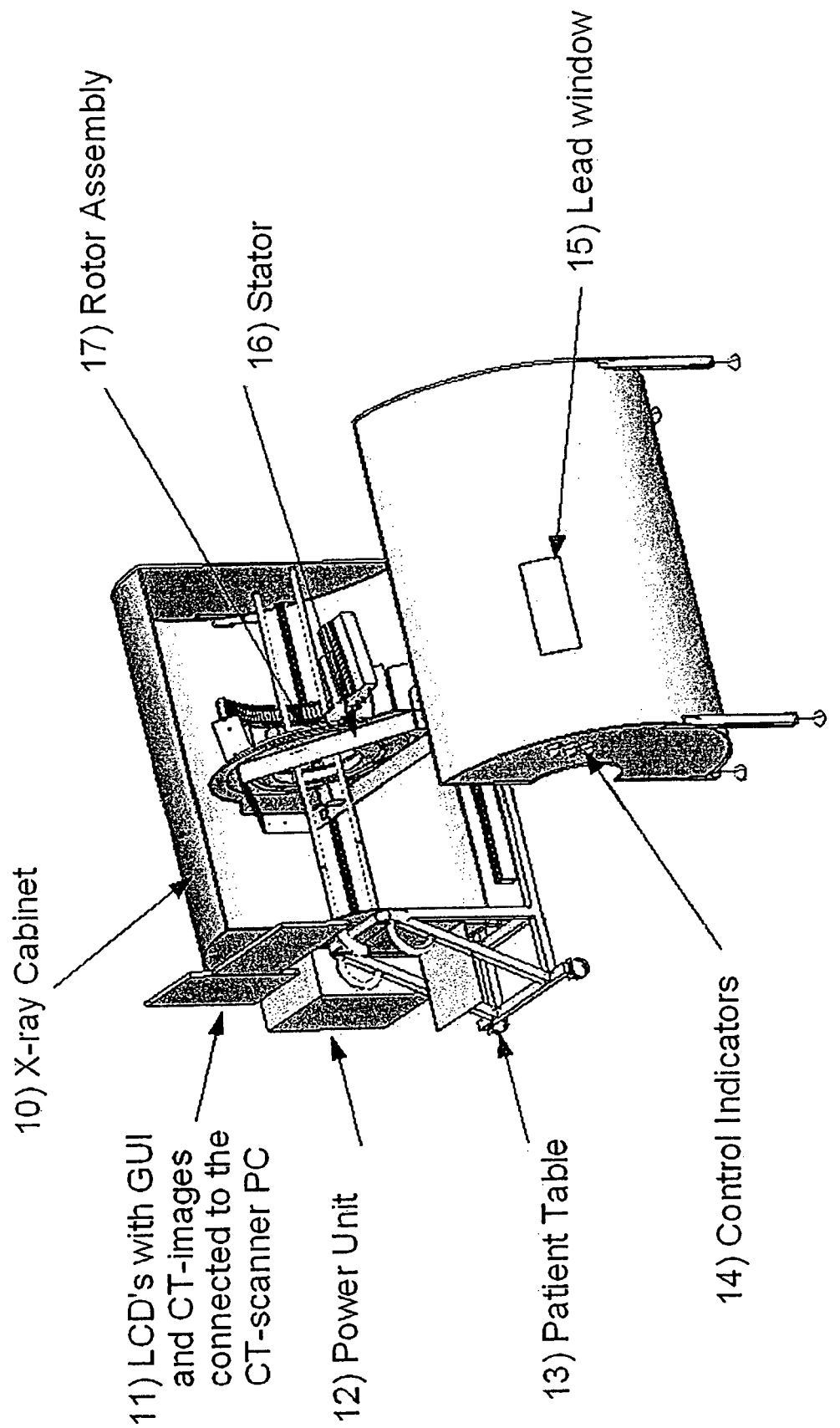
FIG. 1 is a schematic perspective overview of a CT scanning system according to an embodiment of the invention.

An embodiment of a CT scanner according to the present invention, which scanner may be used as a veterinary CT-scanner, is shown in FIG. 1. The CT scanner of FIG. 1 comprises an x-ray cabinet 10 with radiation shield. The cabinet 10 is manufactured in two parts for ease of installation and with dimensions, which allows each of the two parts to be moved through a standard office door. The cabinet 10 has a lead window 15 mounted on one side, which makes it possible to observe an animal to be scanned during the scanning process. The CT scanner of FIG. 1 further comprises a gantry with a stator 16 and a rotor assembly 17, where the rotor assembly 17 comprises a rotor plate 30, which rotor plate 30 holds an x-ray tube 31, a high voltage generator 32, and an x-ray camera 33, see FIG. 3. During scanning, the rotor assembly 17 will turn partly around the animal to be scanned while detecting x-rays transmitted through the scanned animal and collecting data representative of the detected x-rays. The stator 16, on which the rotor assembly 17 is mounted, can move in the longitudinal direction (x-direction) of the cabinet 10 on a set of linear bearings 42, see FIG. 4. The CT scanner of FIG. 1 is further provided with a power supply unit 12, see FIG. 6, a near radiation transparent patient table 13, see FIG. 5, and computer hardware and software for control of the scanning process and for processing image data into an image set, which can be diagnosed. Displays, such as Liquid Crystal Display's, LCD's, 11 are arranged at an end of the cabinet 10, with the displays being connected to the computer of the scanner for displaying a Graphic User Interface, GUI, and CT-images. Control indicators 14 are also arranged at the end of the cabinet 10.

Figure 2:
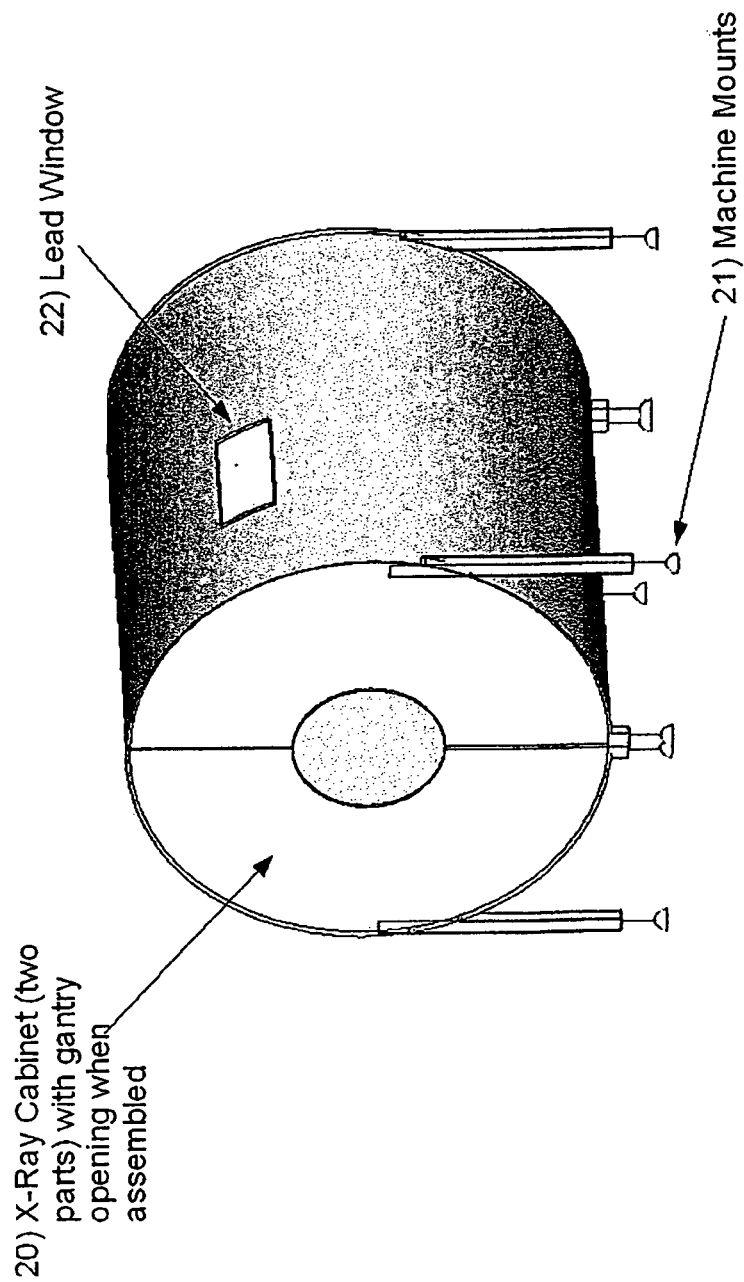
FIG. 2 is a schematic perspective view of an x-ray cabinet according to an embodiment of the invention.

FIG. 2 is a schematic perspective of the x-ray cabinet 10 of the CT scanner of FIG. 1. The x-ray cabinet 20 in FIG. 2 is made of two substantially mirrored parts, where each part is dimensioned to be able to pass through a standard indoor office door. When the cabinet 20 is assembled, there will be a gantry or patient opening, which the patient table 13 fits into, whereby an object or animal, which is laying in the patient table 13 to be scanned, can be moved through the patient opening into the x-ray cabinet 20 for the scanning process. Each of the two parts forming the cabinet 10 has machine mounts 21 for levelling the CT-scanner correct in the clinic and for lifting the cabinet 10 at a distance from the ground floor. A lead window 22 is mounted in the right side of the x-ray cabinet 20 for inspection and observation of the animal during scanning.

According to an embodiment of the invention the cabinet 10, 20 is formed by a framework of aluminium, which is covered by 2 mm of acryl to which is glued a 4 mm lead layer, to thereby form an x-ray shielding layer. On the outside of the lead layer is mounted a plate of 0.5 mm aluminium, which forms the outer surface of the cabinet 10, 20. For this embodiment the cabinet is almost cylindrical with a diameter of 1600 mm and a length of 2100 mm.

The two parts forming the cabinet 10, 20 may be connected together by bolted joints, and the inner surface the joints may be covered by a 4 mm lead layer to secure x-ray shielding.

It is also within an embodiment of the invention that the cabinet 10, 20 is formed by rolled steel with a thickness of around 12-16 mm. On the inner surface, the steel is lined with a lead layer with a thickness of about 1-2 mm, which will depend on the intensity of the x-ray source. Here, the length of the cabinet may be in the range of 1800-2000 mm.

It should be understood that the present invention also covers embodiments, wherein the cabinet 10, 20 is formed by more than two parts, such as for example three or four parts. It is also within embodiments of the invention that the cabinet 10, 20 may have other forms than a cylindrical form. Thus the end parts of the cabinet 10, 20 may have an elliptical, a square, or a rectangular form. It is also within embodiments of the invention that the cabinet may have other dimensions in length, width or diameter, where the dimensions may be selected to suite special needs.

Figure 3:
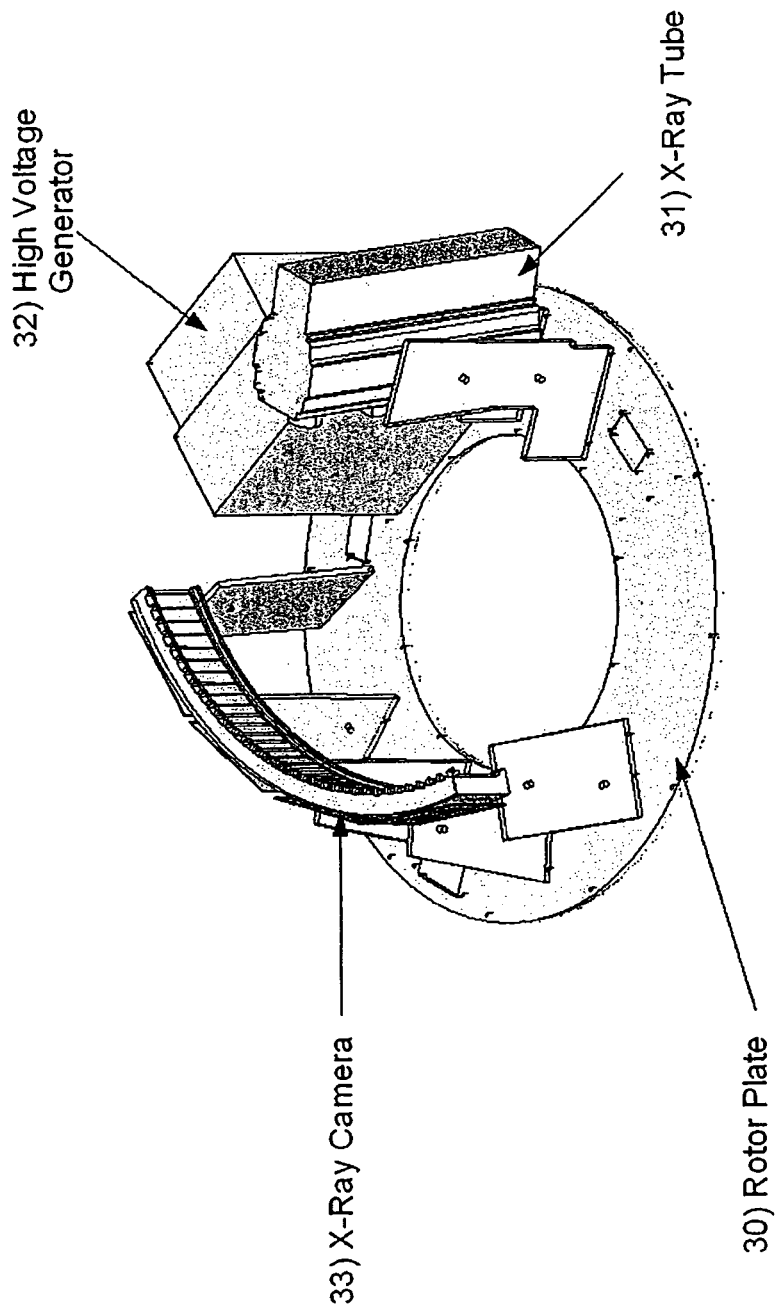
FIG. 3 is a schematic perspective view of a rotor assembly according to an embodiment of the invention, with the rotor assembly comprising x-ray tube, high voltage generator and x-ray camera.

FIG. 3 is a schematic perspective view of a rotor assembly according to an embodiment of the invention. The rotor assembly of FIG. 3 may be used as the rotor assembly 17 for the CT scanner of FIG. 1. The rotor assembly 17 in FIG. 3 comprises a rotor plate 30, on which all the rotating parts are mounted, which include an x-ray tube 31 for generating an x-ray beam, a high voltage generator 32 for generating high voltage for the x-ray tube, and an x-ray camera 33 for collecting the x-ray beam after the beam has passed through the object to be scanned. The collected x-ray beam data are transformed to digital images by the x-ray camera 33 together with supporting computer hardware and software.

According to an embodiment of the invention, the x-ray tube is fed with a voltage of 120 up to kV and a current of up to 16 mA, and the x-ray camera is formed by 31 detector elements, which are arranged in curve having a radius of about 640 mm and covers an angle of about 70°. The gantry or patient opening may have a diameter of around 500 mm.

Figure 4:
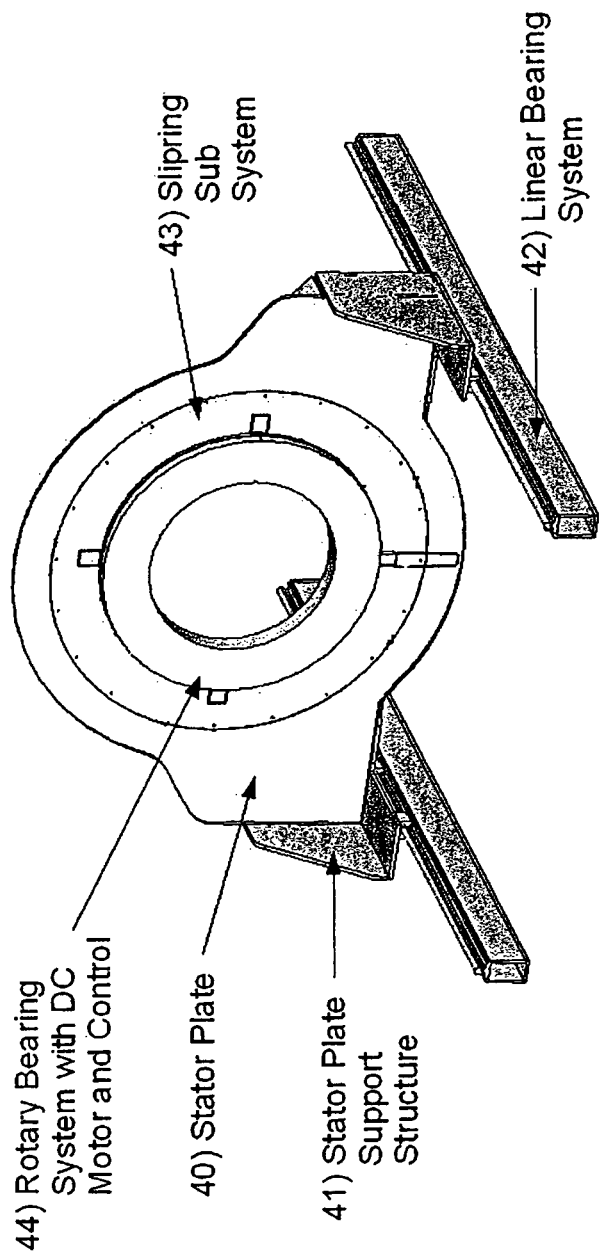
FIG. 4 is a schematic perspective view of a stator according to an embodiment of the invention.

FIG. 4 is a schematic perspective view of a stator according to an embodiment of the invention. The stator of FIG. 4 may be used as the stator 16 for the CT scanner of FIG. 1. The stator 16 of FIG. 4 has a stator plate 40, which is mounted on a support structure 41. The support structure 41 is mounted on a linear bearing system 42, whereby the stator 16 can be moved and positioned in the right positioning in the longitudinal direction. The movement of the stator 16 is driven by a first motor system and controlled from the graphical user interface GUI. A slip-ring subsystem 43 is mounted on the stator 16, which slip-ring system 43 supports power and data transmission from the stator 16 to the rotor assembly 17 and back. A rotary bearing system 44, to which the rotor assembly 17 is mounted, is mounted in the centre of the slip-ring system 43. The rotary bearing system 44 is rotated by a second motor system and controlled from the GUI.

It is preferred that the first motor system is controlled so that the stator 16 is moved in the longitudinal direction of the patient table in successive steps, and that the second motor part is controlled so that the rotor assembly 17 holding the x-ray tube 31 is rotated at an angle of about 180° after each of the movement steps of the stator 16. Hereby, a layered scanning of the object to be scanned can be accomplished. The first motor system may be controlled so that the stator 16 is moved along the patient table in steps of a length being in the range of 10-50 mm, such as in the range of 20-30 mm, such as preferably about 25 mm. The second motor system may be controlled so that rotor assembly 17 and the x-ray tube 31 is rotated at a rotational speed being in the range of 0.3-30 rpm, such as in the range of 0.3-10 rpm, such as in the range of 0.5-5 rpm, such as preferably about 0.7 rpm when performing a scanning operation.

The stator plate 40 of FIG. 4 is made of 10 mm aluminium and has a diameter of 1100 mm. The slip-ring system 43 has two functional parts: slip-rings for the transfer of electrical power (DC 12V, DC 200 V, and AC 220 V) and slip-rings for the transfer of control signals for control of the movement and/or rotation of the rotor assembly 17 and for transfer of interlock signals, see the discussion given in connection with the patient table 13. It is preferred to use wireless data-transmission for transmitting output data from the x-ray camera 33 to the supporting computers.

Figure 5:
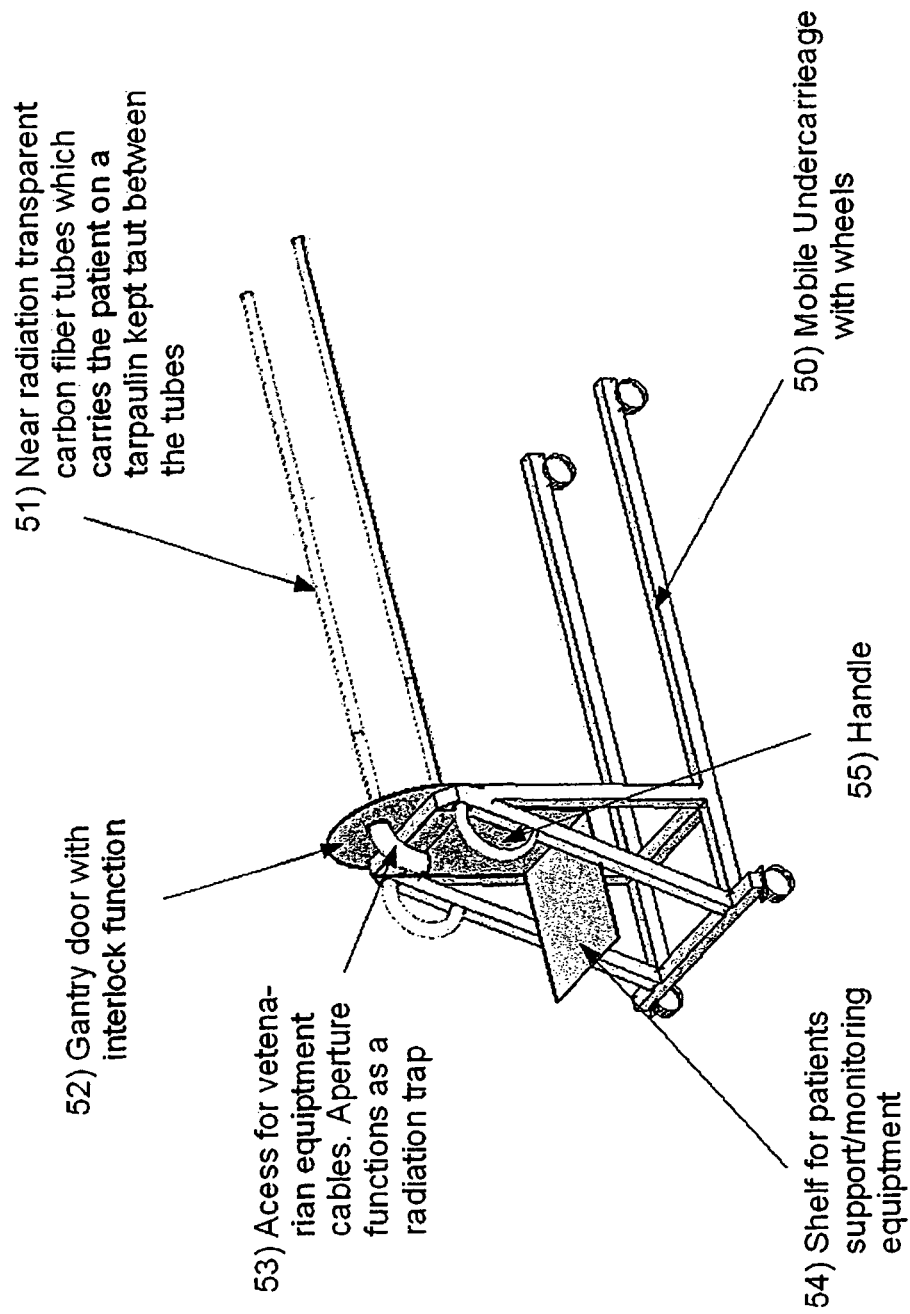
FIG. 5 is a schematic perspective of vies a mobile patient table according to an embodiment of the invention.

FIG. 5 is a schematic perspective of vies a mobile patient table according to an embodiment of the invention. The patient table of FIG. 5 may be used as patient table 13 for the CT scanner of FIG. 1. The mobile patient table 13 in FIG. 5 has two near radiation transparent carbon fiber tubes 51 with a tarpaulin for holding an object or animal to be scanned being arranged and kept taut between the two carbon fiber tubes 51. The two carbon fiber tubes 51 are mounted on an undercarriage with wheels 50. A gantry door or closure part 52 with an interlock function is mounted to the mobile undercarriage 50 at one end of the carbon fiber tubes 51. When the patient table comprising the carbon fiber tubes and the tarpaulin 51 is fully moved into the x-ray cabinet 10 through the gantry or patient opening, and the lower part of the undercarriage 50 is positioned beneath the x-ray cabinet 10,20, the gantry or closure door 52 functions as a radiation shield, and only in this position the interlock function is activated and the CT-scanner can by used. An aperture or opening leading into an x-ray shielded pipe 53 is provided in the closure door 52, whereby cables can pass from the object or animal to be scanned inside the x-ray cabinet 10 to the outside of the cabinet 10, where veterinary equipment may be placed on a shelf 54 mounted to the undercarriage 50. Two handles 55 are mounted at the undercarriage 50 at the same end as the closure door 52. The handles 55 may be used by a veterinary when moving the patient table.

The undercarriage 50 may be formed in steel, and the carbon fiber tubes 51 may have an outer diameter of 47.69 mm and an inner diameter of 40 mm. The carbon fiber tubes may be made of Araldite® LY 556/Aradur® 917-Araldite® and Hardener Accelerator DY 070.

The interlock function may be obtained by a magnetic contact, which is active only when the patient table 13 is correctly arranged in the x-ray cabinet and the closure part fully closes the patient opening in the x-ray cabinet 10, 20.

The gantry or closure door 52 may be lined on the inner surface with a lead layer having a thickness of 4 mm to secure x-ray shielding.

It is within one or more embodiment of the invention that the x-ray cabinet 10, 20 has one or more access panels, where the access panel(s) are designed to be removed or opened for maintenance or service purposes and require tools to be opened.

It is preferred that x-ray cabinet 10, 20 follows the cabinet safety requirements set out in the performance standards for ionizing radiation emitting products sec. 1020.40 Cabinet x-ray systems: 21 CFR 1020.40, which is hereby included by reference.

For the above-described embodiment of a CT scanner, the x-ray shielding is obtained by use of lead as shielding material, but other x-ray shielding materials such as tungsten may be used in accordance with the principles of the invention.

Figure 6:
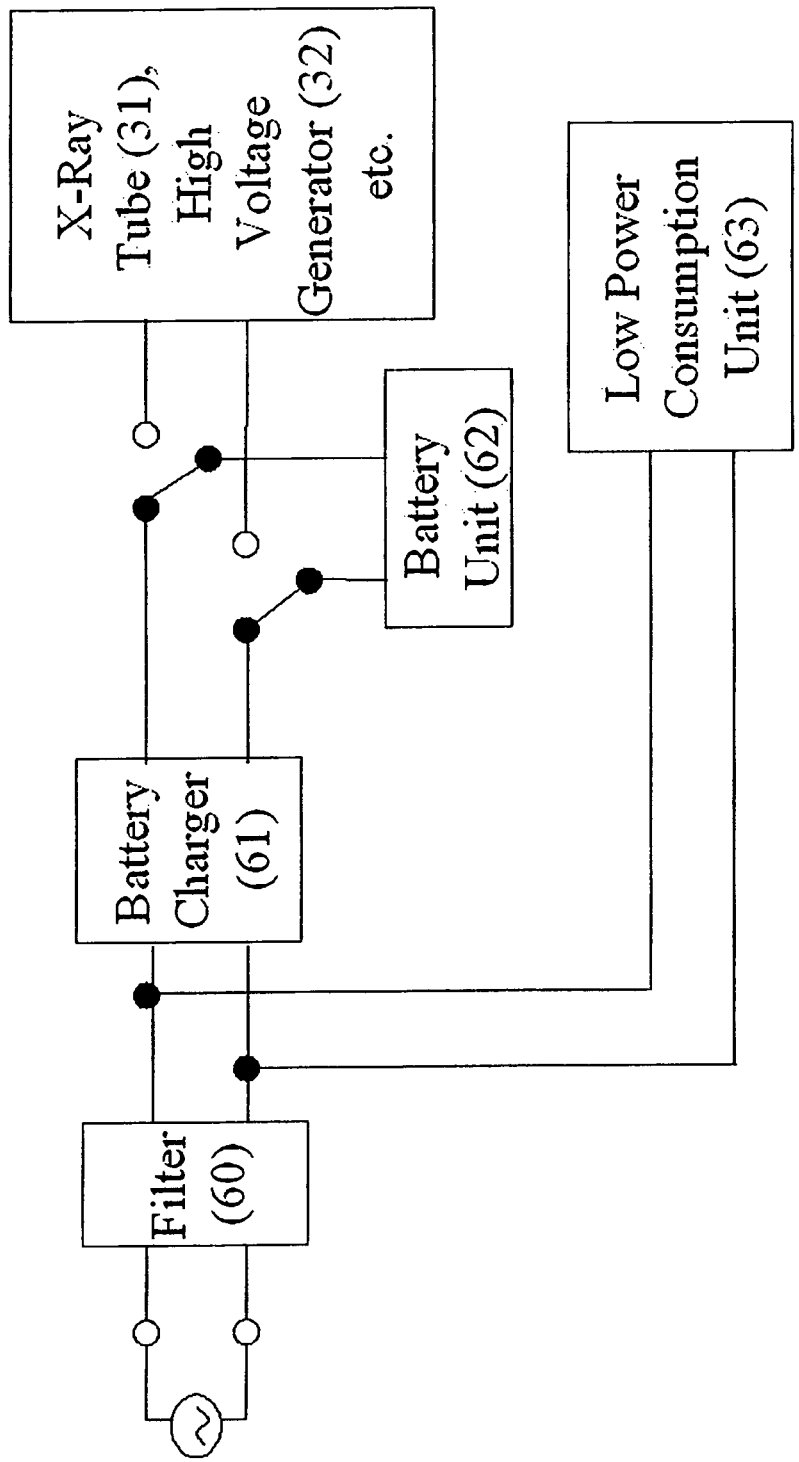
FIG. 6 is a block diagram illustrating a power supply unit according to an embodiment of the invention.

FIG. 6 is a block diagram illustrating a power supply unit according to an embodiment of the invention. The power supply unit of FIG. 6 may be used as the power supply unit 12 for the CT scanner of FIG. 1. The power supply unit 12 of FIG. 6 has a filter section 60, which protects the CT-scanner from external electrical interference. The power supply unit 12 further has a computer controlled battery charger 61 for charging and maintaining batteries of a battery unit 62. The battery unit 62 supplies the base voltage for the high voltage generator 32, which again provides the high voltage for the x-ray tube 31. The power supply unit also comprises a low power consumption unit 63, which supplies power for the low power consumption parts of the CT scanner such as computers, monitors, etc.

The battery unit 62 may comprise a number of rechargeable batteries, such a lead type batteries, NiCd batteries or Li-ion batteries. According to an embodiment of the invention the battery unit 62 comprises 16 12 V rechargeable lead type batteries.

Figure 7:
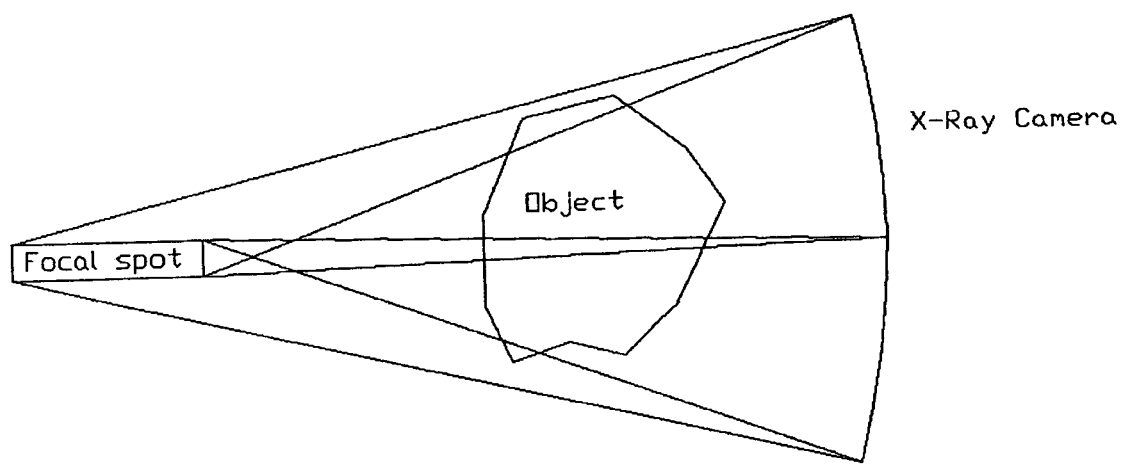
FIG. 7 is a schematic drawing illustrating the arrangement of the focal spot in an x-ray tube according to an embodiment of the invention.

FIG. 7 is a schematic drawing illustrating the arrangement of the focal spot in an x-ray tube 31 relative to the arrangement of the object to be scanned and the x-ray camera 33, according to an embodiment of the invention. For the focal spot of FIG. 7, a camera pixel arranged away from the centre of the camera will "see" a larger focal spot than the ones at the centre of the camera. The dimension of the focal spot may be chosen so that the system is working optimal in the centre with a decrease of the CT resolution out to the rim of the reconstructed image. In a "normal" system the focal spot may be circular and have an equal size at different angles viewed from the detector. For the system of FIG. 7, the focal spot is chosen to have a rectangular shape with the smallest side viewed from the centre line going from the focal spot through the isocenter of the CT reconstructed image to the mid point of the detector element of the x-ray camera 31.

Method of Operation

The method of operation of a CT scanner when scanning an animal according to an embodiment of the invention is described bellow in a number of steps covering from start up and calibration to executing the next CT-scanning to shutting down the CT-scanner.

A) Power Unit Charging:

When the CT-scanner is turned on, the power supply unit will start charging the batteries.

The CT-scanner is equipped with a number of batteries, battery unit 62, which are able to supply power to the x-ray tube 31 during scanning.

B) Start Up and Calibration First Time Each Day:

When the batteries 62 are charged the x-ray tube 31 is ready to deliver an x-ray beam based on the kV and mA settings. A phantom may be placed on the patient table 13, and the patient table 13 is moved into the CT-scanner and the interlock function is activated. Then the CT-scanner will make a CT-scan of the phantom and based on that make the necessary calibration of the CT-scanner.

C) Preparation and Placement of the Animal:

The anesthetized animal is placed on the patient table 13 with supply of oxygen, CO2 monitoring, heart-rate monitoring etc. The animal will be supported and fixed to lie in right position on the patient table 13 with foam rubber and Velcro belts. After this, the patient table 13 is moved into the CT-scanner and the interlock function is activated. Now the CT-scanner is ready to perform a CT-scan of the animal.

D) Scout Scan (Scout X-Ray Image):

When the veterinary decides to CT-scan an animal, he or she already has an idea why a CT-scanning will be valuable for the diagnosis and thereby what part of the animal that should be CT-scanned. But to determine in more details what to scan, the veterinary may perform a scout scan before performing the actual CT-scanning.

E) Positioning of Stator and Rotor in the Right X-Position:

When the scout CT-scanning is performed and the veterinary has decided exactly what to CT-scan, then the stator 16 and rotor 17 is positioned in the first of one or several positions in the longitudinal direction.

F) Final CT-Scan and Data Processing:

Then the final CT-scanning may be performed and the CT scanner computer with scan software will perform the data processing resulting in 3-dimensional reconstruction and high resolution images, upon which the veterinary can base the final diagnostic.

G) Surgery or Wake Up:

When the CT-scanning is finished, the patient table 13 will be removed from the CT-scanner, and the animal will stay anesthetized if the diagnostic concludes a surgery. Otherwise the animal will be placed in a safe place for wake up.

H) Next CT-Scan or Shutting Down the CT-Scanner:

If another CT-scanning has to be performed, the steps above from step C to step G will be repeated with a new animal. Otherwise the power will be turned of and the scanner will shut down.

While the invention has been particularly shown and described with reference to particular embodiments, it will be understood by those skilled in the art that various changes in form and details may be made therein without departing from the spirit and scope of the invention, and it is intended that such changes come within the scope of the following claims.

The invention claimed is:

1. A CT scanning system comprising:
a bed or couch on which an object to be scanned is resting during a scanning operation;
a gantry comprising an x-ray source configured to irradiate an x-ray beam while at least partly rotating about an object being arranged on the bed or couch in order to be scanned, said gantry further comprising an x-ray detector configured to receive x-rays penetrating through the object to be scanned and further configured to provide output signals representative of the received x-rays;
an x-ray cabinet comprising x-ray shielding material and fully surrounding said bed or couch and said gantry, said x-ray cabinet having a first end part with a patient opening allowing introduction of a patient into the x-ray cabinet through said patient opening; and
a closure part or door for providing an x-ray shielding closure of the patient opening at the first end part;
wherein the bed or couch is supported by a mobile undercarriage, whereby the bed or couch can be moved into and out of the patient opening or door.

2. A CT scanning system according to claim 1, wherein the closure part or door is connected to a first end part of the bed or couch.

3. A CT scanning system according to claim 2, wherein the closure part or door and the mobile undercarriage are connected to the first end part of the bed or couch.

4. A CT scanning system according to claim 1, wherein the x-ray cabinet is arranged at a support structure to thereby be lifted at a distance above a ground floor, and wherein the mobile undercarriage or a lower part of the mobile undercarriage is configured to be positioned beneath the x-ray cabinet when the bed or couch is moved into the patient opening and arranged inside the x-ray cabinet.

5. A CT scanning system according to claim 1, wherein the bed or couch comprises at least two carbon fiber tubes for support of the object to be scanned.

6. A CT scanning system according to claim 5, wherein the bed or couch comprises a tarpaulin extending between the two carbon fiber tubes for support of the object to be scanned, and wherein the bed or couch has an elongated form.

7. A CT scanning system according to claim 1, wherein the x-ray cabinet is substantially tubular or cylindrical.

8. A CT scanning system according to claim 1, wherein the x-ray cabinet has first and second oppositely arranged end wall parts, and wherein the patient opening is arranged in the first of said oppositely arranged end wall parts.

9. A CT scanning system according to claim 1, wherein the x-ray cabinet has a window formed by an x-ray shielding material.

10. A CT scanning system according to claim 1, wherein the x-ray cabinet is formed by at least two parts.

11. A CT scanning system according to claim 10, wherein the x-ray cabinet is formed by two substantially mirrored parts, each of said mirrored parts holding about half of the patient opening or door.

12. A CT scanning system according to claim 1, wherein the patient opening has a width or a diameter of at least 200 mm or of at least 400 mm.

13. A CT scanning system according to claim 1, wherein the x-ray cabinet has a width or a diameter of at least 700 mm and not larger than 2500 mm, and wherein the x-ray cabinet has a length of at least 600 mm and not larger than 3000 mm.

14. A CT scanning system according to claim 1, wherein the x-ray cabinet is supported by a number of machine mounts for levelling the x-ray cabinet.

15. A CT scanning system according to claim 1, wherein the closure part or door is provided with an interlock function being active only when the closure part or door is in a closing position relative to the patient opening or door of the x-ray cabinet.

16. A CT scanning system according to claim 15, wherein an x-ray scanning function can be performed only when the interlock function is active.

17. A CT scanning system according to claim 1, further comprising:
- a battery charger for receiving electrical power from an external power source, and for providing a regulated DC power signal;
- a rechargeable battery assembly for storing electrical energy received via the regulated DC power signal; and
- a high voltage generator for supplying electrical power to the x-ray source during a scanning operation; said rechargeable battery assembly being adapted for supplying electrical energy to the high voltage generator during the scanning operation.

18. A CT scanning system according to claim 1, further comprising a linear moving system for moving the gantry along a substantial portion of the bed or couch, and in a direction substantially perpendicular to a rotational movement direction of the x-ray source.

19. A CT scanning system according to claim 18, wherein the CT scanning system is adapted for performing a scanning operation while rotating the x-ray source about the bed or couch during a time period when there is no movement of the gantry by the linear moving system.

20. A CT scanning system according to claim 19, wherein the linear moving system is adapted for moving the gantry along the bed or couch in successive movement steps, and wherein the CT scanning system is adapted for performing a scanning operation after each said movement steps, whereby a layered scanning of the object to be scanned can be accomplished.

* * * * *

UNITED STATES PATENT AND TRADEMARK OFFICE
CERTIFICATE OF CORRECTION

PATENT NO. : 8,540,425 B2  Page 1 of 1
APPLICATION NO. : 12/996334
DATED : September 24, 2013
INVENTOR(S) : Gorm Nielsen Groot It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 345 days.

Signed and Sealed this
Fifteenth Day of September, 2015

Michelle K. Lee
*Director of the United States Patent and Trademark Office*